United States Patent
Chung

(10) Patent No.: US 7,155,754 B2
(45) Date of Patent: *Jan. 2, 2007

(54) PORTABLE HYGIENIC WATER JET HAVING SANITARY DISPOSABLE NOZZLE PROTECTOR ON NON-DISPOSABLE NOZZLE

(75) Inventor: Jing-Yau Chung, Houston, TX (US)

(73) Assignee: JYC International, Inc., Houston, TX (US)

(*) Notice: Subject to any disclaimer, the term of this patent is extended or adjusted under 35 U.S.C. 154(b) by 230 days.

This patent is subject to a terminal disclaimer.

(21) Appl. No.: 10/873,092

(22) Filed: Jun. 22, 2004

(65) Prior Publication Data

US 2004/0231041 A1  Nov. 25, 2004

Related U.S. Application Data

(62) Division of application No. 10/325,994, filed on Dec. 19, 2002, now Pat. No. 6,751,813.

(60) Provisional application No. 60/377,858, filed on May 4, 2002, provisional application No. 60/366,117, filed on Mar. 20, 2002, provisional application No. 60/352,925, filed on Jan. 29, 2002.

(51) Int. Cl.
*A47K 3/26* (2006.01)

(52) U.S. Cl. .................... 4/443; 604/310; 222/323; 222/401

(58) Field of Classification Search .................. 4/443; 604/118, 146, 151, 257, 263, 279, 310; 222/323, 222/401; 239/104, 602

See application file for complete search history.

(56) References Cited

U.S. PATENT DOCUMENTS

| 2,613,111 A | * | 10/1952 | Freund et al. ......... 222/323 X |
|---|---|---|---|
| 2,619,086 A | | 11/1952 | Wylde ..................... 604/257 |
| 3,653,377 A | | 4/1972 | Rebold ................ 604/153 X |
| 3,731,676 A | | 5/1973 | Rebold ................ 604/151 X |
| 3,762,411 A | | 10/1973 | Lloyd et al. .............. 604/151 |
| 3,773,046 A | | 11/1973 | Roseberg ................. 604/151 |
| 3,783,867 A | | 1/1974 | Slummersby et al. ... 604/151 X |
| 4,178,931 A | | 12/1979 | Lind et al. ................ 604/151 |
| 4,234,127 A | | 11/1980 | Tada et al. ................ 239/333 |
| 4,259,754 A | | 4/1981 | Bader et al. ................ 4/443 |
| 4,622,704 A | | 11/1986 | Chung ......................... 4/443 |
| 4,772,274 A | * | 9/1988 | Lukacs ................. 604/279 X |
| 4,890,340 A | | 1/1990 | Lovitt ......................... 4/443 |
| 5,030,211 A | * | 7/1991 | Zakroczymski ........... 604/262 |
| 5,090,067 A | | 2/1992 | Cogdill .................... 4/420.2 |
| 5,097,540 A | | 3/1992 | Lovitt ......................... 4/443 |
| 5,241,712 A | | 9/1993 | Mahoney ................ 4/420.2 |
| 5,295,274 A | | 3/1994 | Daniels et al. ............. 4/443 |
| 5,371,993 A | | 12/1994 | Saito ....................... 52/245.1 |
| 5,754,988 A | | 5/1998 | Presa ........................ 4/443 |
| 5,792,109 A | | 8/1998 | Ladd ........................ 604/151 |
| 5,864,895 A | | 2/1999 | Ota et al. ................... 4/443 |
| 6,751,813 B1 | | 6/2004 | Chung ........................ 4/443 |

* cited by examiner

*Primary Examiner*—Robert M. Fetsuga
(74) *Attorney, Agent, or Firm*—Mark A. Oathout

(57) ABSTRACT

A device for producing a jet of water has a portable handheld water reservoir to be filled with warm or cold water manually by the user, a battery powered handheld air or water pump to create water pressure for the generation of water jet which is delivered through a handheld nozzle system, a thin flexible disposable nozzle protector for sanitary protection of the non-disposable nozzle and nozzle tip, and an optional new medicine dispenser on the nozzle system.

14 Claims, 5 Drawing Sheets

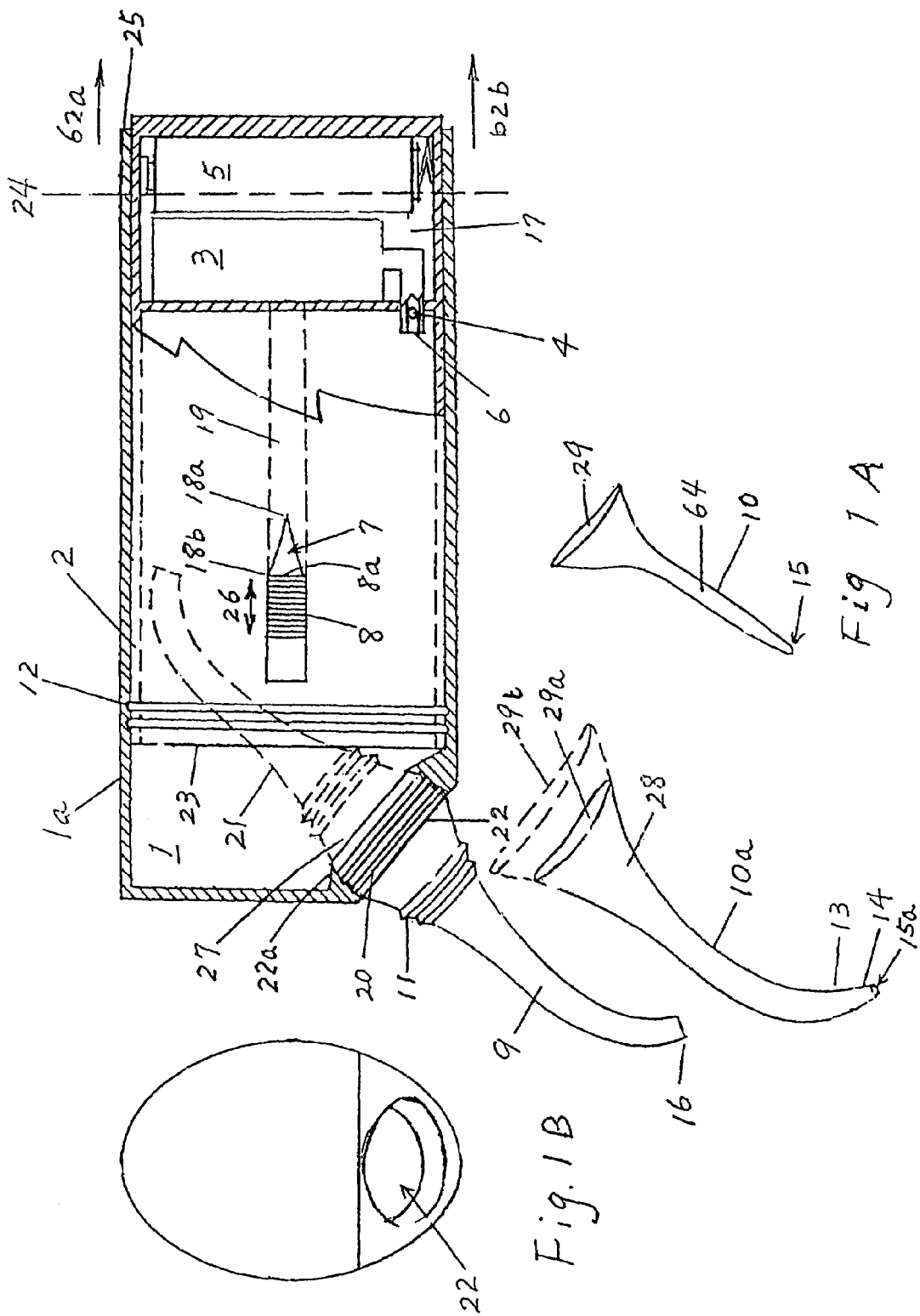

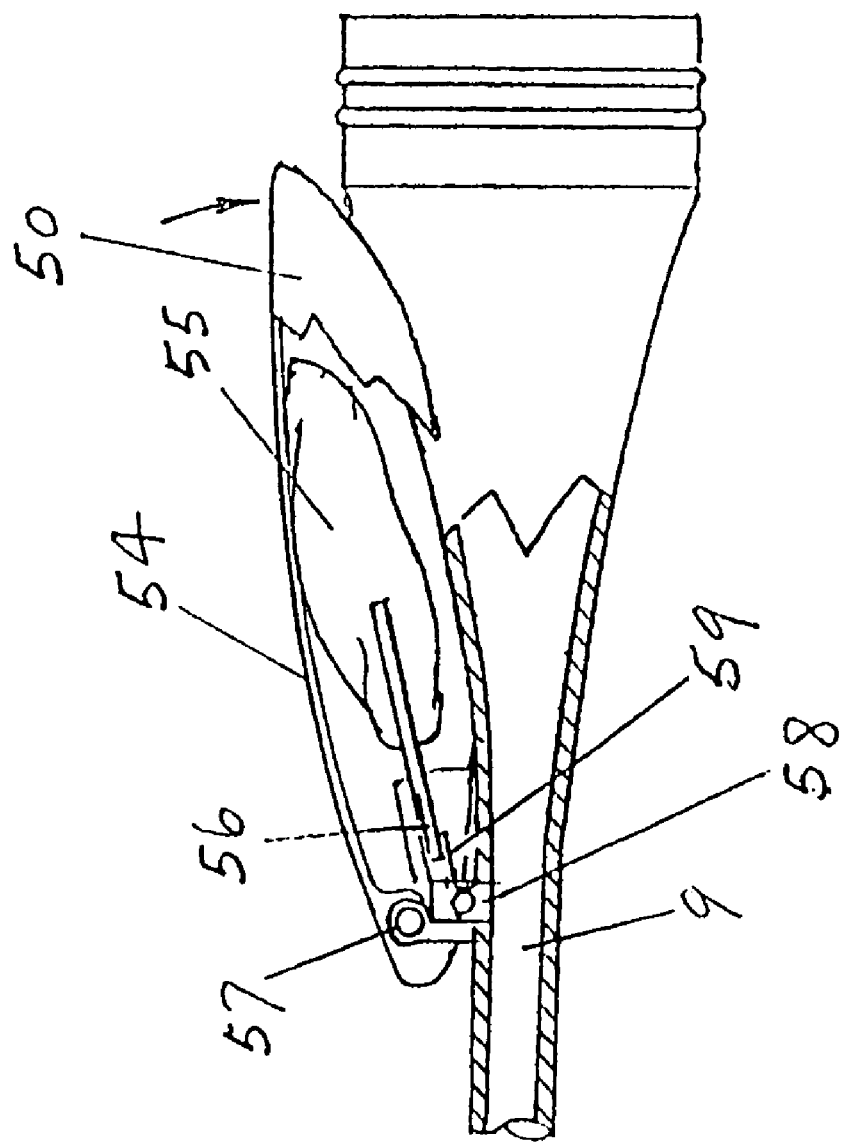

PORTABLE HYGIENIC WATER JET HAVING SANITARY DISPOSABLE NOZZLE PROTECTOR ON NON-DISPOSABLE NOZZLE

CROSS-REFERENCE TO RELATED APPLICATIONS

This application is a divisional of U.S. Utility patent application Ser. No. 10/325,994 filed Dec. 19, 2002 (U.S. Pat. No. 6,751,813) which is based upon U.S. provisional patent applications Nos. 60/352,925, filed Jan. 29, 2002; 60/366,117, filed Mar. 20, 2002 and 60/377,858, filed May 4, 2002, and claims the benefit of all of same.

STATEMENTS REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Description of the Related Art

The current invention is an improvement over the U.S. Patent, "Portable Hygienic Warm Water Jet Having Disposable Nozzle Tip" issued to the current inventor on Nov. 18, 1986 (U.S. Pat. No. 4,622,704). The above-mentioned patent will be referred to as "the existing Patent" hereafter.

The existing Patent involves a portable bidet with a heating means providing warm water for cleansing the lower torso of the human body using a disposable nozzle, which delivers a stream of warm water jet to the body.

BRIEF SUMMARY OF THE INVENTION

The current improvements over the existing Patent include the uses of (a) a portable handheld water reservoir to be filled with warm or cold water manually by the user, (b) a battery powered handheld air or water pump to create water pressure for the generation of water jet which is delivered through a handheld nozzle system, (c) a thin flexible disposable nozzle protector for sanitary protection of the non-disposable nozzle and nozzle tip. (d) an optional new medicine dispenser on the nozzle system.

BRIEF DESCRIPTION OF THE SEVERAL VIEWS OF THE DRAWINGS

For a fuller understanding of the invention, the following drawings are provided in conjunction with the detail descriptions of the invention which will be presented in the next section:

FIG. 1A is a semi-cross sectional view of the preferred embodiment of the present invention showing two options for the sanitary nozzle protector.

FIG. 1B is a side view of the preferred embodiment shown in FIG. 1A.

FIG. 4 is an illustration of the optional medicine dispenser.

DETAILED DESCRIPTION OF THE INVENTION

Figure 1C:
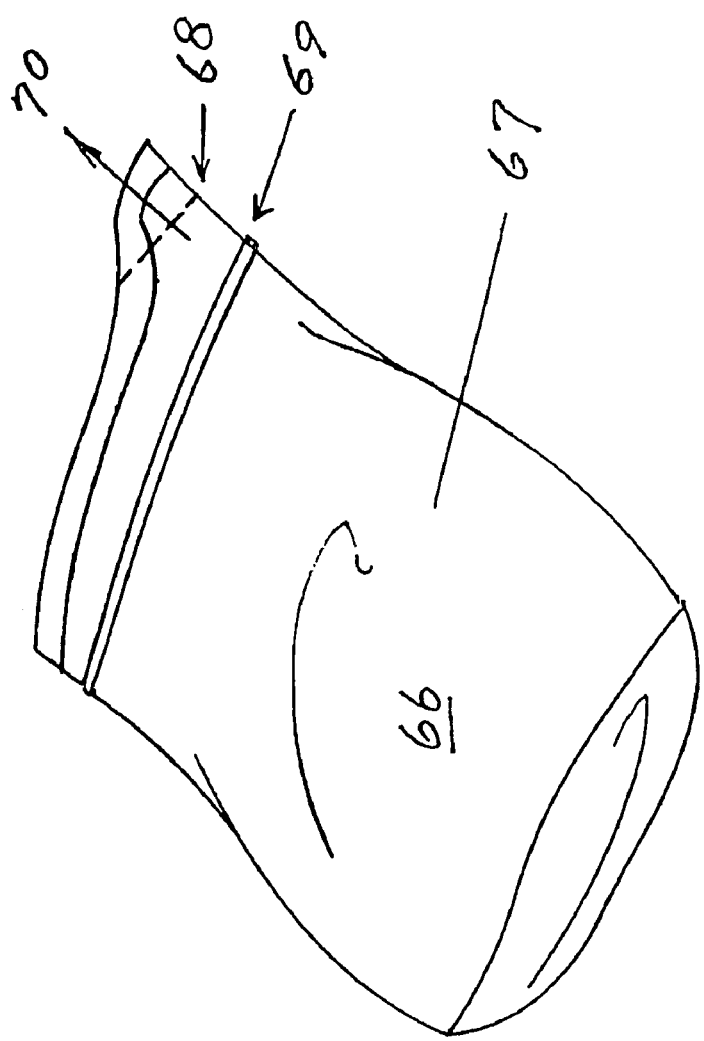
FIG. 1C is an illustration of an example of packaged water to be used to fill the water reservoir.

With reference to FIGS. 1A and 1B, the present invention includes a handheld water reservoir 1 which is formed by the combined inner cavity of shell 1a and the inner cavity of shell 2. Both shell 1a and shell 2 have the same cross sectional shape, such as a circular cross section, or an elliptical cross section as depicted in FIG. 1B. The cross section of shell 1a is slightly larger than that of shell 2, such that shell 1a can enclose shell 2 leaving a small gap between the inner wall of shell 1a and the outer wall of shell 2. Reservoir 1 has its minimum volume, when shell 1a encloses shell 2 entirely as depicted in FIG. 1A. Reservoir 1 has its maximum volume when shell 2 extends outward to its limit in the direction indicated by the arrows 62a and 62b. As shown in FIG. 1A, shell 2 has one or more than one "O" ring 12 at its opened end 23. When shell 2 is sliding out of shall 1a in the direction indicated by the arrows 62a and 62b, a cavity with an increasing combined volume of the inner cavities of shell 1a and shell 2 is formed. Consequently, this cavity, which is airtight between the inner wall of shell 1a and the outer wall of shell 2, forms the water reservoir 1 with variable water capacity. Said water capacity depends on the amount of the outward extension of shell 2. A stop (not shown) is provided on the inner edge of the opened end 25 of shell 1a, such that the outward extension of shell 2 stops when the opened end 23 of shell 2 reaches location 24 which is indicated by a dotted line near the opened end 25 of shell 1a.

Also included in the present invention are, an air pump 3 powered by battery 5, an on-off switch 8 and a nozzle 9 to be covered by a sanitary nozzle protector 10 as depicted in FIG. 1A. The battery 5 can be one or more than one ordinary battery such as the 1.5 volt AA or AAA type battery or it can be one or more than one rechargeable battery. The nozzle 9 can be a straight nozzle or it can be bent at its tip as depicted in FIG. 1A. With "O" rings 20 on the outer wall of nozzle 9, the water reservoir 1 and the nozzle 9 are connected airtight at an opening 22 of shell 1a, as shown in FIG. 1A. The "O" ring can also be installed on the wall of the opening 22. Nozzle 9 can be easily connected and disconnected to water reservoir 1. As depicted by the dotted nozzle contour 21 in FIG. 1A, nozzle 9 can be inserted backward into water reservoir 1 for storage purpose. This feature of storing nozzle 9 inside the water reservoir 1 is important for making a compact overall dimension of the device when the device is not in use, in particular, when the device is carried by the user in a bag or in a suitcase. An optional nozzle cap (not shown) can be used to cover the opening of nozzle 9 when nozzle 9 is in the storage position inside the water reservoir 1. As shown in FIG. 1A, a circular stop 22a having the same center as that of opening 22, is provided at the inner edge of opening 22, such that nozzle 9 will stop at a proper location when it is inserted into opening 22 in either direction. When nozzle 9 is inserted in the operational forward direction, it is stopped, as the nozzle entrance 27 reaches stop 22a, since the entrance 27 is larger in diameter than stop 22a. When nozzle 9 is inserted in the reversed direction, it is stopped by the stop 22a at the location where the nozzle tapering begins. Nozzle 9 can be rotated freely relative to the water reservoir 1 about the central axis of its cylindrical nozzle entrance, when nozzle 9 is installed in opening 22 in the outward direction for operation as shown in FIG. 1A. This central axis of the nozzle entrance coincides with the central axis of the opening 22. This feature of being able to rotate nozzle 9 in the opening 22, provides the user with an option of choosing his or her preferred water jetting angle relative to the handheld water reservoir 1, and hence choosing the preferred water jetting angle relative to his or her hand which holds the device at the water reservoir 1.

As shown in FIG. 1A, the air pump 3 and the other electronics, such as the battery 5 are located in the electronic compartment 17 at the closed end of shell 2. The air pump 3 includes an air inlet opening 7, within the electronic compartment 17 and an air outlet 6 which is connected to the water reservoir 1 as depicted in FIG. 1A. An optional one-way valve 4 is installed inside the outlet 6 as a back-up device to keep the water from flowing from water reservoir 1 to the electronic compartment 17. As will be discussed later, with a special design electronic switch 8, the water will not flow into the electronic compartment 17 through air outlet 6, even if the optional one-way valve 4 is not used, provided the system is working normally.

With reference to FIG. 1A, the electronic on-off switch 8 can be installed in a groove 19 on the outer wall of shell 2. An air inlet line (shown in FIG. 3 as air passageway 38) can be installed inside groove 19 to connect the air inlet opening 7 to the electronic compartment 17. This air inlet line provides air inlet to the air pump inside the electronic compartment 17. Switch 8 is designed to slide along groove 19 back-and-forth in the direction indicated by the arrow 26 shown in FIG. 1A. The size of the opening 7 is determined by the position of switch 8 on opening 7. The size of the opening 7 is the smallest when the edge 8a of switch 8 is at position 18a, while the size of the opening 7 is the largest when the edge 8a is at position 18b. The purpose of creating a variable size of opening 7 is to control the inlet airflow to air pump 3, and hence to control the air pump output volumetric flow rate. The control of the air pump output volumetric flow rate by means of the positioning of switch 8 will be discussed in more detail later with an illustration in FIG. 3. Both switch 8 and groove 19 are flushed with, or below the surface of shell 2, such that they slide under shell 1 a when shell 2 extends outward in the direction shown by the arrows 62a and 62b. After shell 2 extends to a predetermined position, switch 8 will be no longer under shell 1a, and becomes reachable by the users. When the device is not in use, switch 8 is pushed to an "off" position automatically by a spring (shown in FIG. 3 as spring 31). In this position, switch 8 covers the opening 7 completely, and the electronic compartment 17 becomes airtight with a sole air passageway to the water reservoir 1 through outlet 6. Under this condition, the water in the water reservoir 1 will not leak into compartment 17 through outlet 6 due to the pressure balance, regardless of the performance of the back-up one-way valve 4.

With reference to FIG. 1A, prior to operating the device, the user would fill the water reservoir 1 with water through opening 22 before nozzle 9 is installed in opening 22. The user may use warm or cold tap water to fill the water reservoir 1. The user may also fill the water reservoir 1 with a bag or a container of packaged water, or with a combination of tap water and the packaged water. An example of such packaged water is illustrated in FIG. 1C where the packaged water 66 is packed in a plastic bag 67 with a re-closable opening at 69 and a water outlet 70 which is created by cutting off the bag at 68 along the indicated dashed line. The packaged water 66 can be water with or without fragrant. It can be water with soap or medication; The packaged water can also be a concentrated solution packaged in a bottle with a dropper.

After nozzle 9 is installed in opening 22, nozzle 9 will be completely or partially covered by the sanitary nozzle protector 10. The entire device will then be rotated up side down such that nozzle 9 will be at the bottom. When the air pump 3 is on, the air pressure pushes the water in water reservoir 1 out to nozzle 9, provided that nozzle 9 is at the predetermined operational location below the water reservoir 1. It should be noted that air pump 3 can be located either above or below the water reservoir 1.

Figure 2:
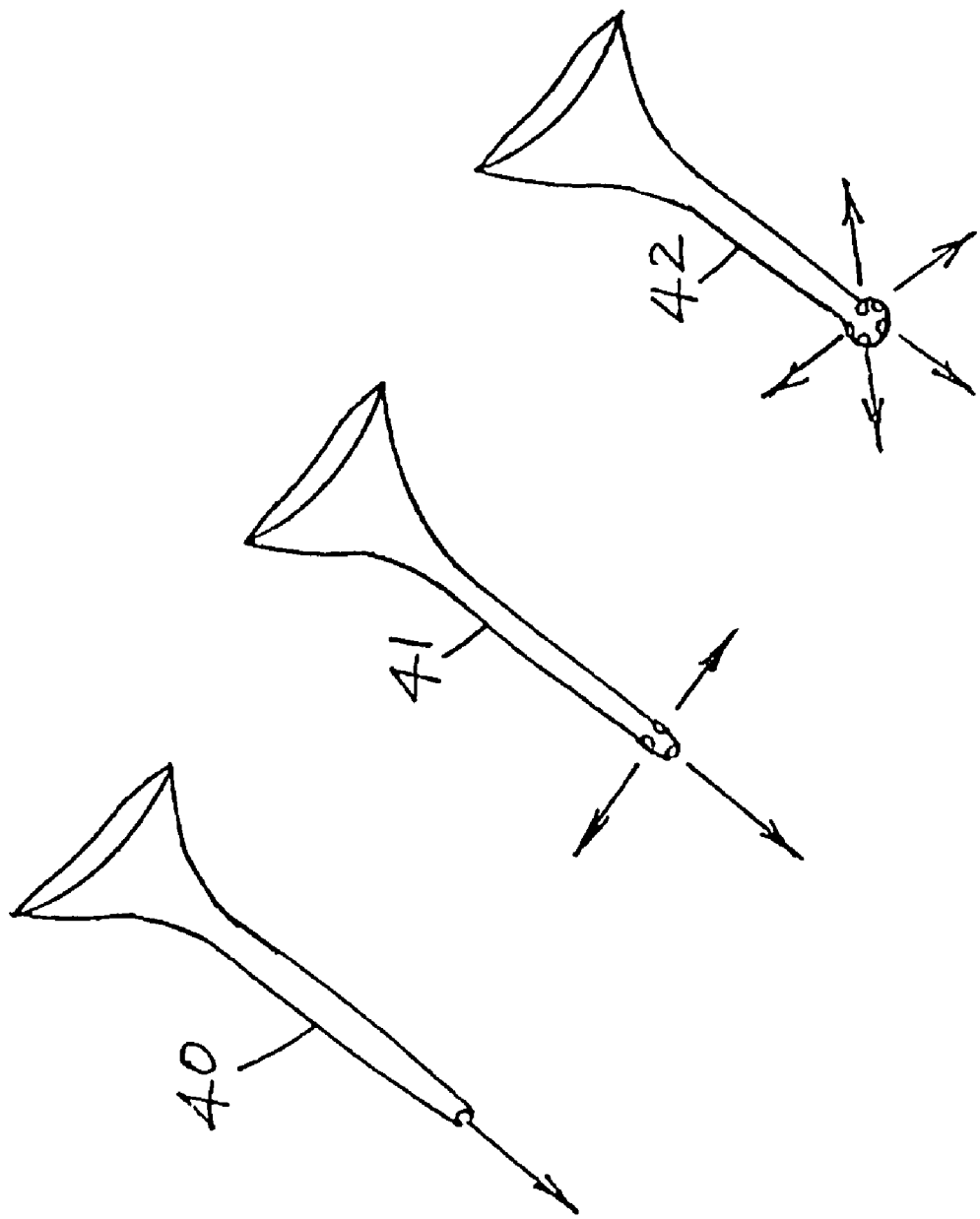
FIG. 2 is an illustration of examples of the nozzle protector configurations.

Similar to a balloon or surgical glove with openings at two ends, the original shape of the sanitary nozzle protector 10, before it is expanded to cover nozzle 9, can be a small thin-wall tubing 64 with a relatively large opening 29 (having a conical shape) as shown in FIG. 1A. At the other end 15, there is one or more than one small hole for releasing the water. When the sanitary nozzle protector 10 is expended and cover nozzle 9, its overall shape becomes similar to that of nozzle 9 with the opening 29a as indicated by the nozzle protector 10a in FIG. 1A. When the device is in use, nozzle 9 is completely or partially covered by the sanitary nozzle protector 10a such that the potentially contaminated water bouncing back from the user's body will not contaminate nozzle 9 or any nozzle tip as part of nozzle 9. The sanitary nozzle protector can be extended to cover and to protect a portion of the water reservoir 1, which connects to nozzle 9. In this case, the sanitary nozzle protector is made longer and with larger opening 29b. The water that is delivered from the tip of nozzle 9 is released from a small hole on end 15a of the sanitary nozzle protector 10a as depicted in FIG. 1A. The sanitary nozzle protector 10 can be made of a thin flexible soft material, such as latex, thin plastic or paper, and is designed to be disposable after use. Unlike a solid nozzle or a solid nozzle tip, a flexible soft sanitary nozzle protector 10 can be flatten and packed in layers with other sanitary nozzle protectors occupying relatively small storage space. The cost of a sanitary nozzle protector can be substantially less than that of a solid nozzle or a solid nozzle tip. One or more nozzle protector fastener 11 can be provided on nozzle 9 as shown in FIG. 1A to catch the sanitary nozzle protector 10a at about location 28 and to hold the sanitary nozzle protector 10a tightly on nozzle 9. A hook (not shown) can also be installed on nozzle 9 to catch the sanitary nozzle protector 10a, and to fasten the protector on the nozzle. When the sanitary nozzle protector 10a is in place, covering nozzle 9, the end 16 of nozzle 9 is located under position 13 of the sanitary nozzle protector 10a. The sanitary nozzle protector 10a is extended beyond position 13 to position 14 to ensure a complete protection of nozzle 9 at the tip. The extended portion also provides a soft contact to the user's body, in case the nozzle system touches the user's body accidentally. The sanitary nozzle protector 10 can be designed to provide various water spraying patterns. Three examples of the sanitary nozzle protector creating three different water spraying patterns are shown in FIG. 2, where the nozzle protector 40 is designed to spray water with a single water jet in the forward direction, and the nozzle protector 41 provides water jets in side ways in addition to a single forward jet as shown by the arrows, while the nozzle protector 42 sprays water in all directions. The sanitary nozzle protector makes possible to provide variety of nozzle spray patterns by the use of a single non-disposable nozzle.

Figure 3:
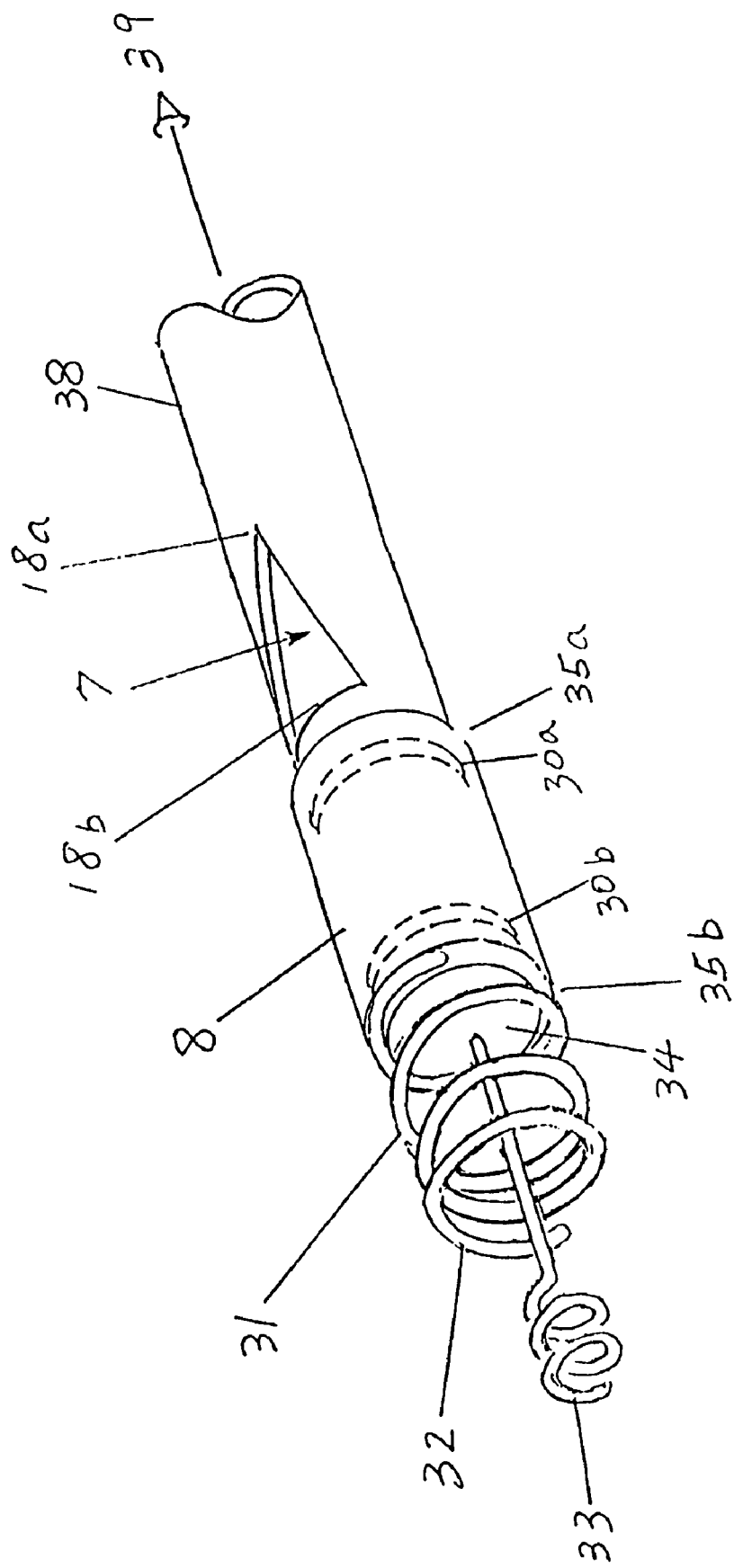
FIG. 3 is an illustration of the electronic switch that controls the pumping capacity of the air pump and the strength of the water jet.

As mentioned earlier, the user can control the amount of air inlet to the air pump 3 by properly positioning switch 8, and hence controlling the size of opening 7 as depicted in FIG. 1A. The less air being fed into air pump 3 from opening 7, the less the pumping capacity of air pump 3, and hence less water is delivered to nozzle 9. The opposite is true until the air pump capacity reaches its maximum. FIG. 3 illustrates an example of the mechanism of switch 8 that controls the airflow and hence controls the strength of the water jet delivered through nozzle 9.

As shown in FIG. 3, the switch system includes a cylindrical switch 8 which slides on a cylindrical air passageway 38 as shown. The air passageway 38 has an approximately triangular shaped opening 7 as shown in FIG. 3, with the end 18a having a narrower opening and the end 18b having a wider opening. The change in the width of the opening 7 can be linear, exponential or in any other way. One end of the air passageway 38 is connected without air leak to the electronic compartment 17 as indicated by an arrow 39 in FIG. 3. The other end of 38 is closed, making opening 7, the only air inlet to air pump 3, since the electronic compartment 17 is sealed airtight at any other location on its walls except at the air outlet 6. As depicted in FIG. 3, optional "O" rings 30a and 30b are installed on the inner wall of switch 8 ensuring no air leakage between the inner wall of switch 8 and the outer wall of air passageway 38. With reference to FIG. 3, when the device is not in use, spring 31 pushes switch 8 to an "off" position. At this position, both edge 35a and "O" ring 30a are located slightly beyond location 18a, while both edge 35b and "O" ring 30b are located slightly beyond location 18b. With this switch "off" position, the opening 7 is completely covered by switch 8 without air leak. Both switch 8 and air passageway 38 can be made to a tight clearance such that any air leak through their inter face becomes negligible even without "O" rings 30a and 30b. When the device is in use, the user moves switch 8 along 38 in the direction from locations 18a to 18b. As depicted in FIG. 3, a spring-loaded rod 33 is placed at the close vicinity of the closed end 34 of switch 8 when the switch is at the "off" position. The end 34 is made of a conductor material. When the end 34 contacts 33, after a slight initial displacement of switch 8, the end 34 contacts both spring 32 and spring 33, which are connected one-to-one to two opened ends (not shown) of the DC circuit, hence the electrical circuit is closed. The user can choose to position edge 35a at any location between 18a and 18b, while the circuit is closed and the DC power is on. The closer the edge 35a is to 18b, the more airflow is allowed to flow into the opening 7, and hence the bigger the air pump output. This results in a stronger water jet delivered from nozzle 9.

The air pump 3 can be replaced by an optional water pump (not shown). In this case, the water pump shall be placed at the other end of the water reservoir 1, such that the water in the water reservoir 1 will be above the water pump during operation. In operation, the water flows into the water pump through an inlet (not shown) by means of the gravitational force before it is pumped to nozzle 9. The advantages of using an air pump, that is preferred in the present invention, as compared to using an optional water pump, are:

(1) Using an air pump, the water in the nozzle can be pushed out completely at the normal pumping speed during the final stage of pumping. Using a water pump, however, the water in the nozzle cannot be pumped out at the normal pumping speed during the final stage of pumping. Because after the water reaches a level below the water pump location, the water pump can no longer pump out the water in the nozzle which is located below the water pump. Therefore, the water in the nozzle can only flow out mostly by the gravitational force rather than the water pump pressure.

(2) Proper nozzle designs, such as the nozzle 9 configuration shown in FIG. 1A, can be feasibly adopted only in the case an air pump is used in the system. The tapered nozzle shown in FIG. 1A minimizes the backpressure with special converging cross sectional areas of the nozzle channel. Such nozzle holds relatively large amount of water, due to its relatively large entrance area. With the air above the water, an air pump can push all the water out of the nozzle at the normal pumping speed during the final stage of pumping. If a water pump is used, however, a relatively large amount of water will be left un-pumped in the nozzle, for the reason explained above. The only feasible nozzle configuration for a system using a water pump will be the one with a non-tapered small passageway to minimize the un-pumped water. Such water passageway, however, creates relatively high backpressure, and it requires a pump with a relatively large capacity to overcome such backpressure in order to maintain a proper water flow.

(3) As an optional application of the device, the user can continue to blow the air through the nozzle system for a drying purpose, after the water is pumped out completely, provided a larger capacity air pump is used. This air-drying option is not obtainable, if a water pump is used in the system.

(4) The air pump can be installed on either side of the water reservoir. The water pump, however, can only be installed on the lower side of the operational position of the water reservoir, giving a restriction in the design of the device.

Shown in FIG. 4 is an optional medicine dispenser 54, which includes a cover 50 and a medicine bag 55. A straw 56 is extended from inside bag 55 to the outside of the bag. The straw 56 is heat sealed to the opening of bag 55 such that the medicine can only be dispensed through straw 56. In operation, straw 56 is inserted to a hole 59, which is connected to nozzle 9 through a one-way valve 58. The one-way valve allows the medicine to flow into nozzle 9, but to keep the water from flowing into straw 56 from nozzle 9. The cover 50 is hinged to nozzle 9 at hinge 57. A spring (not shown) is used at hinge 57 to force the cover 50 turning towards the direction of nozzle 9. When cover 50 is pressed by the user in the direction indicated by the arrow, a controlled amount of medicine in bag 55 is pushed into nozzle 9 through the straw 56, the hole 59 and the one-way valve 58.

Certain variations may be made to the preferred embodiment as would be known to one of ordinary skill in the art without departing from the spirit of the invention.

What is claimed is:

1. A portable apparatus for producing a jet of water, comprising:
   a shell having an internal reservoir wherein the shell having the internal reservoir has a handheld size;
   a nozzle connected to the shell and to the reservoir;
   a protector for fitting over the nozzle;
   a pump mounted in the shell; and
   a medicine dispenser connected to the nozzle.

2. A portable apparatus for producing a jet of water, comprising:
   a shell having an internal reservoir wherein the shell having the internal reservoir has a handheld size;
   a nozzle connected to the shell and to the reservoir;
   a protector for fitting over the nozzle;

a pump mounted in the shell; and a switch for the pump mounted on the shell wherein the switch includes a means for controlling the strength of the jet of water.

3. A portable apparatus for producing a jet of water, comprising:

a shell having an internal reservoir wherein the shell having the internal reservoir has a handheld size;

a nozzle connected to the shell and to the reservoir;

a protector for fitting over the nozzle;

a pump mounted in the shell wherein the pump is an air pump; and a battery powered electronic compartment mounted in the shell for powering said air pump.

4. The apparatus according to claim 3, wherein said protector comprises a tubular body having an interior adaptable for fitting over the nozzle, a first opening on one end and a second opening proximate another end.

5. The apparatus according to claim 4, wherein the first opening on said tubular body is relatively larger in area than the second opening.

6. The apparatus according to claim 5, wherein the first opening has a conical shape.

7. The apparatus according to claim 4, wherein said protector is made of a thin, expandable, pliable soft material.

8. The apparatus according to claim 3, wherein said protector is a sanitary protector.

9. The apparatus according to claim 3, further including a switch for the pump mounted on the shell.

10. The apparatus according to claim 3, wherein the nozzle connected to the shell includes a means for disconnecting the nozzle from the shell.

11. The apparatus according to claim 3, wherein the nozzle is a spout and said protector has a first opening on one end and a second opening proximate another end; and wherein the first opening is relatively larger than the second opening.

12. The apparatus according to claim 3, further including a container for filling the reservoir, wherein the container has a volume of water.

13. The apparatus according to claim 12, wherein the container is a bag.

14. The apparatus according to claim 12, wherein the container further includes a volume of a substance selected from the group of substances consisting of a fragrance, a medicine, and a soap.

* * * * *